United States Patent [19]

Tomoda

[11] Patent Number: 4,770,181

[45] Date of Patent: Sep. 13, 1988

[54] GAS STREAM BLOWER FOR NON-CONTACT TYPE TONOMETER

[75] Inventor: Hideo Tomoda, Tokyo, Japan

[73] Assignee: Tokyo Kogaku Kikai Kabushiki Kaisha, Tokyo, Japan

[21] Appl. No.: 899,595

[22] Filed: Aug. 25, 1986

[30] Foreign Application Priority Data

Aug. 29, 1985 [JP] Japan .................................. 60-191251

[51] Int. Cl.$^4$ .............................................. A61B 3/16
[52] U.S. Cl. ...................................... 128/648; 417/553
[58] Field of Search ................... 128/645, 648 F, 652; 417/553 X, 562, 570, 415 X

[56] References Cited

U.S. PATENT DOCUMENTS

| | | | |
|---|---|---|---|
| 2,084,665 | 6/1937 | Aikman | 417/553 X |
| 2,377,916 | 6/1945 | Anderson | 417/553 |
| 2,764,098 | 9/1956 | Dickey et al. | 417/553 X |
| 3,018,779 | 1/1962 | Tyler et al. | 417/553 X |
| 3,585,849 | 6/1971 | Grolman | 128/648 |
| 3,752,604 | 8/1973 | Dorn | 417/553 X |
| 3,894,817 | 7/1975 | Majoros et al. | 417/415 |
| 4,374,330 | 2/1983 | Fey | 417/415 X |

Primary Examiner—Edward M. Coven
Attorney, Agent, or Firm—Finnegan, Henderson, Farabow, Garrett and Dunner

[57] ABSTRACT

A gas stream blower for non-contact type tonometer comprises a cylinder, a piston arranged in the cylinder to divide the interior thereof into an air open chamber and a compression chamber, a nozzle communicated with the compression chamber such that air in compression chamber is compressed by advancing the piston toward the compression chamber and thus the compressed air is blown toward an eye-examining position through the nozzle, a first one way valve which is fitted in the piston and is closed at the time of air compressing, and a second one way valve which is provided in the midway of a communicating path between the compression chamber and the nozzle and is opened when the pressure of the compressed air is higher than a predetermined value.

8 Claims, 3 Drawing Sheets

FIG. 4
(PRIOR ART)
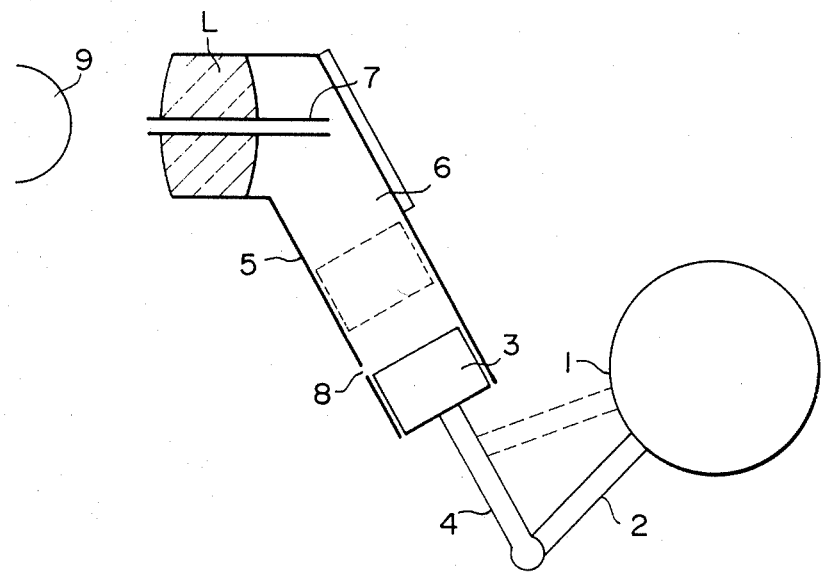
FIG. 5
(PRIOR ART)
FIG. 6
(PRIOR ART)
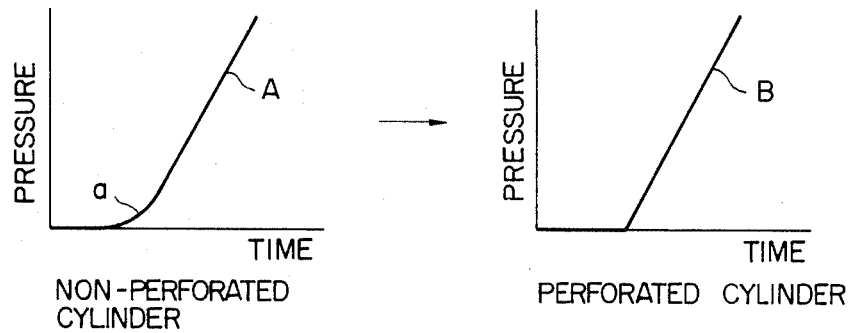
NON-PERFORATED CYLINDER
PERFORATED CYLINDER

GAS STREAM BLOWER FOR NON-CONTACT TYPE TONOMETER

BACKGROUND OF THE INVENTION (1) Field of the Invention:

The present invention relates to a gas stream blower of a non-contact type tonometer in which a compressed air stream is blown upon an eye to be examined to deform a cornea of the eye, a physical amount indicative of this deformation and a pressure of the fluid are detected, and an eye pressure is determined from the correlation between the physical amount and the fluid pressure.

(2) Prior Art Statement:

For instance, an apparatus shown in FIG. 4 has been heretofore known as a gas stream blower for the non-contact type tonometer of this kind.

According to this gas stream blower, an arm 2 of a rotary solenoid 1 is connected to a piston rod 4 integrated with piston 3 and a compression chamber 6 of a cylinder 5 in which the piston 3 is arranged to communicated with a nozzle 7. The axis of this nozzle is directed to an eye-examining position. This apparatus is so designed that when electric current is passed through the rotary solenoid 1, the arm 2 is turned clockwise, while when electric current is cut, the arm 2 is returned to its original state by means of a spring force of a spring (not shown). At the lower portion of the cylinder 5 is formed an air escape hole 8 for escaping air from the compression chamber 6 at a compression initial stage.

In such a construction, when the arm 2 is turned clockwise by actuating the rotary solenoid 1, the piston 3 is displaced upwardly through the piston rod 4. Thereby, the pressure in the compression chamber 6 becomes higher, so that air in the compression chamber 6 is blown upon the eye 9 to be examined at the eye-examining position from the nozzle 7.

At this time, the change rate of the moving speed of the piston 3 is large at the actuating initial stage of the rotary solenoid 1, that is, at the time of the compression starting. Thus, if no air escape hole 8 is provided in the cylinder 5, the pressure in the compression chamber 6 varies in a curve fashion at the time of the compression starting as in an a portion of a pressure-varying line A in FIG. 5. However, when the air escape hole 8 is provided in the cylinder 5, air in the compression chamber 6 escapes to the outside through the air escape hole 8 at the compression start initial stage. Consequently, the pressure in the compression chamber 6 linearly varies at the time of compression starting as in a pressure-varying line B of FIG. 6.

Therefore, when the gas stream blower shown in FIG. 4 is used, the air stream of which pressure linearly varies can be blown upon the eye to be examined through the nozzle 7.

However, such a gas stream blower has the following disadvantages:

(1) In this gas stream blower, when electric current to the rotary solenoid 1 is cut after the air stream is blown upon the eye 9 to be examined, the rotary solenoid 1 is returned to its original state by a spring force of the spring not shown and the piston 3 is displaced downwardly. Thereby, the pressure in the compression chamber 6 lowers, so that air near the eye 9 to be examined is sucked into the compression chamber 6 through the nozzle 7. Thus, air which is sucked into the compression chamber 6 at the air-sucking time is blown upon an eye of a next person to be examined.

However, when air stream is blown upon the eye 9 to be examined in such a manner, tear is scattered from the eye 9 to be examined, so that the scattered tear is sucked into the compression chamber 6 through the nozzle 7 after the air blowing and is blown upon the eye to be examined of the next person. Hence, such is not hygienically favorable.

(2) Further, since the piston 3 is driven by the rotary solenoid 1 provided with the arm 2 in the above-mentioned gas stream blower, the rotary solenoid 1 is arranged on the side of the cylinder 5. Therefore, the gas stream blower becomes larger in the horizontal direction, which is not favorable in making the whole apparatus compact.

(3) In addition, since the cylinder 5 and the nozzle 7 are rigidly and integrally combined through an objective lens L, vibrations of the rotary solenoid 1 at the time of compression are transmitted to the nozzle. However, when the vibrations are transmitted to the nozzle 7, a position where air stream is blown upon the eye 9 to be examined is deviated, so that there occurs a problem that accurate measurement is impossible.

(4) Moreover, in order that the change in the pressure of the air stream blown upon the eye 9 to be examined may be linearly done, the air escape hole 8 has been conventionally provided. Thus, when the air escape hole 8 is communicated with the compression chamber 6 by downwardly displacing the piston 3 as mentioned above and the piston 3 is further downwardly displaced, contaminated air in the exterior is sucked into the compression chamber 6. Consequently, this contaminated air is blown upon the eye to be examined, which is not hygienically favorable.

SUMMARY OF THE INVENTION

It is therefore an object of the present invention to provide a gas stream blower for a non-contact type tonometer in which tear scattered from an eye to be examined is not sucked into a compression chamber through a nozzle at the time of air being sucked into.

In order to accomplish this object, the present invention relates to a gas stream blower for a non-contact type tonometer a gas stream blower for a non-contact type tonometer comprising: a cylinder body; a piston slidably arranged in the cylinder body to divide the interior thereof into an air open chamber and a compression chamber; a first one way valve which is adapted to allow flowing of air only from said air open chamber to said compression chamber and is closed by a pressure within the compression chamber when air within the compression chamber is compressed; a nozzle for blowing a compressed air within the compression chamber toward an eye-examining position; a communicating path communicating said compression chamber and said nozzle; and a second one way valve which is so provided on the midway of said communicating path as to allow flowing of air toward a side of said nozzle only and is opened when the pressure of the compressed air within the compression chamber becomes higher than a predetermined value.

According to such a construction, since the first one way valve is closed when the piston is displaced toward the compression chamber, air in the compression chamber is compressed. Then, when the pressure in the compression chamber reaches the predetermined value, the second one way valve is opened to blow the air in the compression chamber upon the eye-examining position through the nozzle.

On the other hand, when the piston is returned to its original state after the air-blowing, the first one way valve is opened and at the same time the second one way valve is closed, so that air is sucked into the compression chamber from the side of the air open chamber of the cylinder.

An advantages of this invention is that tear scattered from the eye to be examined can be assuredly prevented from being sucked into the compression chamber through the nozzle at the time of the air being sucked into.

Furthermore, when the piston is driven forward or rearward by the linear actuator arranged coaxially with the cylinder on the side of the air open chamber, the whole construction can be made compact.

Moreover, when the compression chamber and the nozzle are communicated together by means of the flexible tube, even if vibrations of the piston-driving source act upon the cylinder, the vibrations are absorbed by the flexible tube and not transmitted to the nozzle. Thus, the nozzle is not vibrated, and the air stream blown from the nozzle is accurately blown upon the desired location of the eye to be examined at the eye-examining position.

These and other objects, features and advantages of the present invention will be well appreciated upon reading of the following description of the invention when taken in conjunction with the attached drawings with understanding that some modifications, variations and changes of the same could be made by the skilled person in the art to which the invention pertains without departing from the spirit of the invention or the scope of claims appended hereto.

BRIEF DESCRIPTION OF THE DRAWINGS

For a better understanding of the invention, reference is made to the attached drawings, wherein;

FIG. 4 is a schematic illustration view of a prior art gas stream blower for a non-contact type tonometer; and FIGS. 5 and 6 are pressure characteristic diagrams of the prior art gas stream blower for the non-contact type tonometer.

DETAILED DESCRIPTION OF THE PREFERRED EMBODIMENT

In the following, an embodiment according to the present invention will be explained with reference to FIGS. 1-3.

Figure 1:
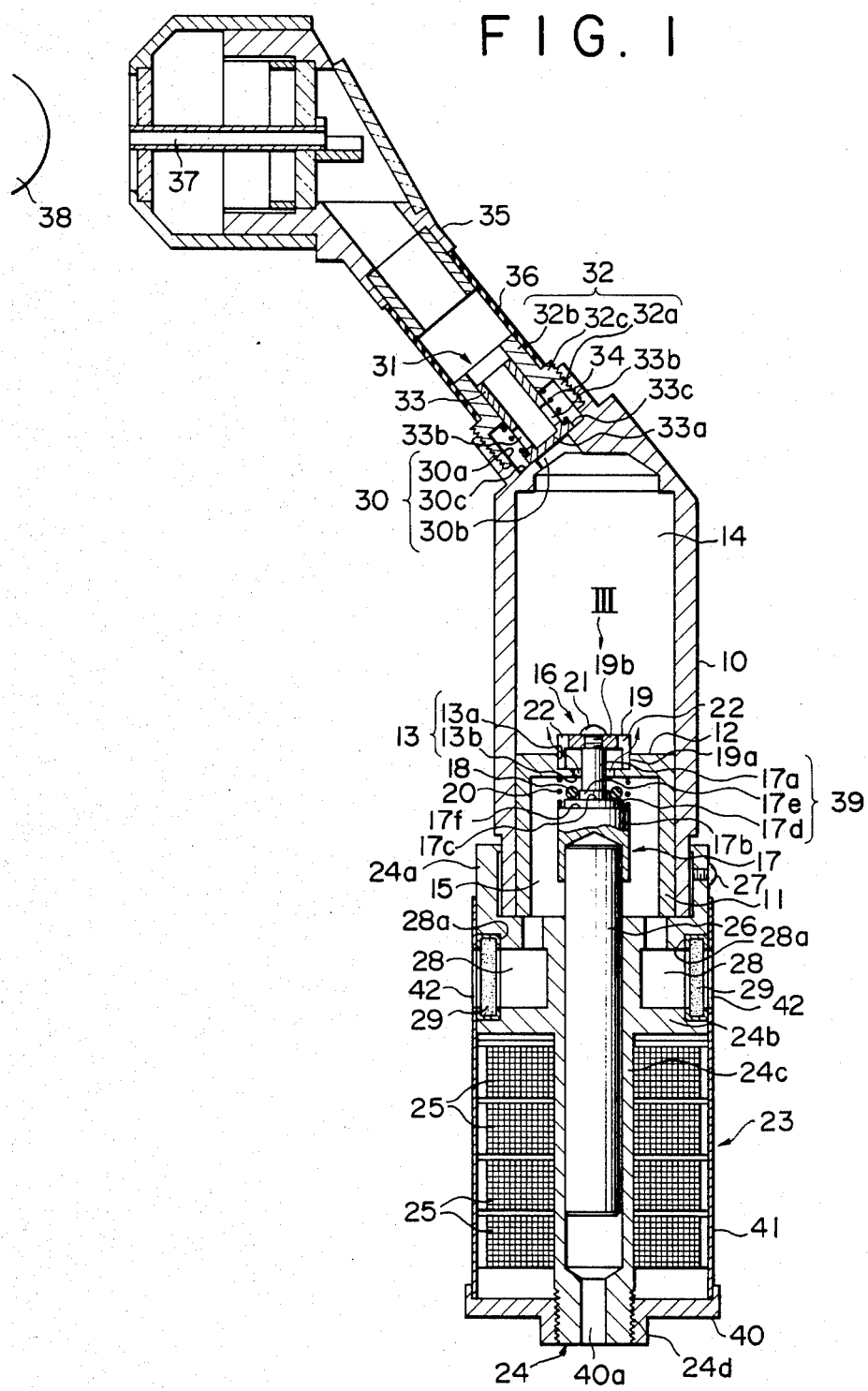
FIG. 1 is a sectional view of a gas stream blower for a non-contact type tonometer showing one embodiment according to the present invention.
Figure 2:
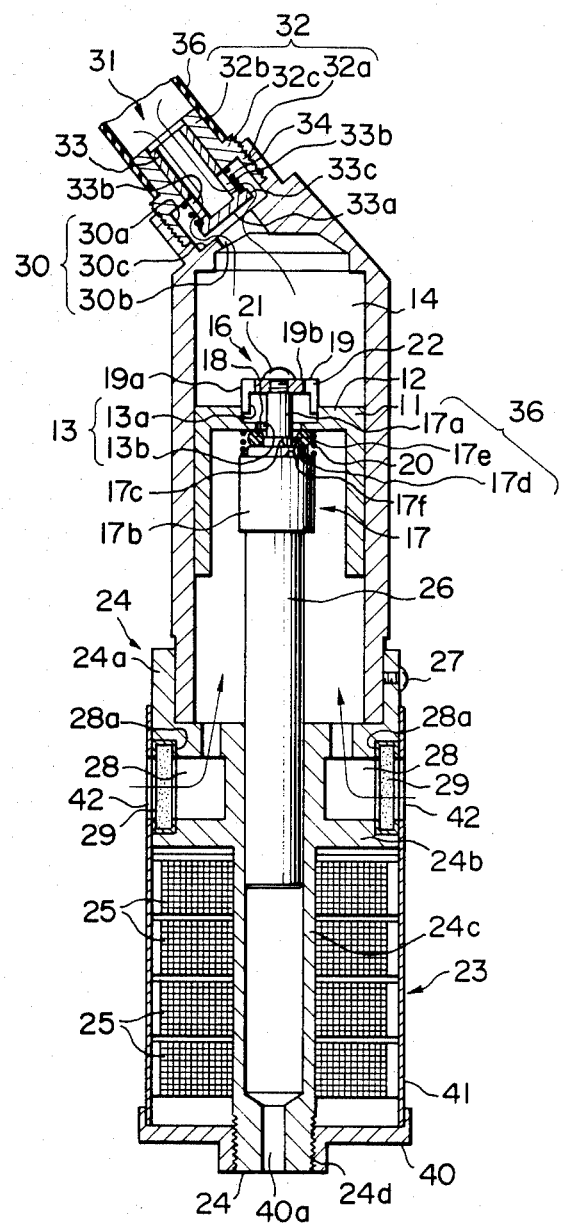
FIG. 2 is a partial sectional view of the gas stream blower shown in FIG. 1 in an operated state.
Figure 3:
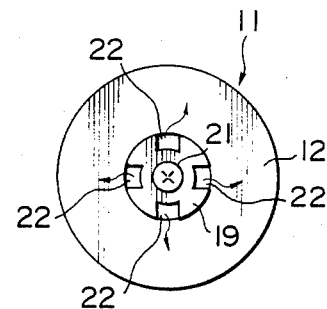
FIG. 3 is a plane view of a piston of FIG. 1 as viewed from a III direction.

In FIGS. 1-2, reference numeral 10 is a cylinder of a gas stream blower 11, denotes a cylindrical piston arranged in the cylinder 10 an end wall, 12 is closing one end of the piston 11, and a stepped hole 13 provided as a valve hole at the central portion of the end wall 12. Reference numeral 13a is a large diameter hole portion and 13b denotes a small diameter hole portion of the stepped hole 13. The piston 11 divides the interior of the cylinder 10 into a compression chamber 14 and an air open chamber 15.

A first one way valve 16 is fitted into the stepped hole 13. This one way valve 16 comprises an axial valve body 17, a seal ring 18, a stopper 19 and a spring 20.

The valve body 17 is constituted by a large diameter cylindrical portion 17b and an axial portion 39 coaxially connected to this large diameter cylindrical portion 17b. The axial portion 39 is constituted by a large diameter axial portion 17d, a medium diameter axial portion 17e, and a small diameter axial portion 17a. The large diameter axial portion 17d is coaxially connected to the large diameter cylindrical portion 17b and is formed in a diameter slightly smaller than that of the large diameter cylindrical portion 17b. The medium diameter axial portion 17e is coaxially connected to the large diameter axial portion 17d and is designed in a diameter slightly smaller than that of the large diameter axial portion 17d. And the small diameter axial portion 17a is coaxially connected to the medium diameter axial portion 17e and is designed in a diameter slightly smaller than that of the meduim diameter axial portion 17e. Between the larger diameter axial portion 17d and the medium diameter axial portion 17e is formed a continuous stepped portion 17c as a seal receipt stepped portion, and a spring receipt stepped portion 17f is formed between the large diameter axial portion 17d and the large diameter cylindrical portion 17b.

The above-mentioned seal ring 18 is fitted around the medium diameter axial portion 17e of the valve body 17. This seal ring 18 abutts to the continuous stepped portion 17c. Further, the above-mentioned spring 20 is interposed between the spring receipt stepped portion 17f and the end wall 12.

The small diameter axial portion 17a is inserted into the stepped hole 13 from the side of the air open chamber 15, and a stopper 19 arranged in the compression chamber 14 is secured to the tip end portion of the small diameter axial portion 17a. This stopper 19 is constituted by a cylindrical portion 19a as a stopper cylindrical portion and an end wall 19b closing an end of the cylindrical portion 19a on the compression chamber side. The stopper 19 is coaxially secured to a tip end of the small diameter axial portion 17a by means of a screw 21. Further, a cylindrical portion 19a of the stopper 19 is fitted to the large diameter portion 13a, movably in the axial direction. A slit 22 for guiding air is formed in this cylindrical portion 19a (see FIG. 3). The slit 22 is extended over the opposite ends of the cylindrical portion 19a, and are formed at four positions of the cylindrical portion 19a at an interval of 90°.

A linear DC motor 23 as a linear actuator is arranged coaxially with the cylinder 10 on the side of the air open chamber 15 of the cylinder 10. This linear DC motor 23 comprises a bobbin 24 made of a non-magnetic material, a coil 25 and a rod 26 made of a permanent magnet. This bobbin 24 is constituted by a cylinder-fitted large diameter cylindrical portion 24a fitted around the outer periphery of an end portion of the cylinder 10 on the air open chamber side, a thick wall cylindrical portion 24b coaxially connected to this cylinder-fitting cylindrical portion 24a, and a coil-fitting smaller diameter cylindrical portion 24c connected coaxially to this thick wall cylindrical portion 24b. A coil 25 is wound around the coil-fitting cylindrical portion 24c. A rod 26 is slidably inserted into the bobbin 24.

Further, the cylinder-fitting portion 24a of the bobbin 24 is secured to the cylinder 10 by means of a screw 27. In the thick wall cylindrical portion 24b of the bobbin 24, a communicating hole or gas suction hole 28 is formed as an air suction hole. The hole 28 is opened inside and at the outer peripheral surface of the cylinder-fitting cylindrical portion 24a to communicate the air open chamber 15 with an atmosphere. One end portion of the communicating hole 28, that is, an end portion of the bobbin on the peripheral surface side is formed with a filter housing stepped hole 28a in which a filter 29 is arranged. A male screw portion 24d is formed at a free end portion of a coil-fitting cylindrical portion 24c of the bobbin 24. An air escape hole 40a is further formed at the free end portion. A cap 40 is screwed to the male screw portion 24d. An outer cylinder 41 as a cover is secured to the cap 40. The outer cylinder 41 covers the bobbin 24 and the coil 25. An opening 42 which is opened to the filter- housing hole portion 28a is formed in the outer cylinder 41, and the above-mentioned filter 29 is held between the outer cylinder 41 and the bobbin 24. One end portion of the rod 26 is fitted and secured into the large diameter cylindrical portion 17. According to such a linear DC motor 23, when the magnetic polarity of the bobbin is made reverse to that of the rod 26 upon energization of the coil 25, the rod 26 is advanced toward the compression chamber 14 by magnetic force, while the magnetic polarity of the bobbin 24 is made identical to that of the rod 26 by reversing the energizing direction of the coil 25, the rod 26 is attached toward the bobbin 24 by the magnetic force.

A stepped air escape opening 30 as an air ejecting opening is provided at an end portion on the side of the compression chamber 14 of the cylinder 10. This air escape opening 30 comprises a large diameter hole portion 30a as a large diameter air ejecting opening and a small diameter portion 30b as a small diameter air ejecting opening as well as a stepped portion 30c between the large diameter hole portion 30a and the small diameter hole portion 30b. A second one way valve 31 is fitted into this stepped air ejecting opening hole 30.

This one way valve 31 comprises a valve cylinder 32, a cylindrical valve body 33, a communicating hole 33b, a spring receipt flange 33c, and a spring 34. The valve cylinder 32 is constituted by a large diameter cylindrical portion 32a on the compression chamber side, a small diameter cylindrical portion 32b on the nozzle side, and a stepped wall 32c connecting the cylindrical portion 32a and the cylindrical portion 32b. The cylindrical valve body 33 is closed by an end wall 33a thereof, and the free end portion of the cylindrical valve body 33 is slidably fitted into the small diameter cylindrical portion 32b. The communicating hole 33b is opened to the periphery of the end portion of the valve body 33 on the compression chamber side. The spring receipt flange 33c is protrusively provided at the outer periphery of the end portion of the valve body 33 on the compression chamber side. And a spring 34 is interposed between the spring receipt flange 33c and the stepped wall 32c.

The cylindrical portion 32a of the valve cylinder 32 on the compression chamber is screwed to the large diameter portion 30a as the large diameter air ejecting hole. Further, the valve body 33 is seated on the stepped portion 30c by means of the spring 34 to close the small diameter portion 30b.

A hollow nozzle fitting member 35 is connected to the small diameter cylindrical portion 32b of the valve cylinder 32 by way of a flexible tube 36 made of rubber, synthetic resin or the like. A nozzle 37 which is extended toward an eye-examining position is fitted into the nozzle fitting member 35. In the figures, a reference numeral 38 is an eye to be examined at the eye-examining position.

Next, the function of the thus constituted gas stream blower for the non-contact type tonometer will be explained.

In such a construction, when the magnetic polarity of the bobbin 24 is reversed to that of the rod 26 by energizing the coil 25 of the linear DC motor 23, the rod 26 is advanced toward the compression chamber 14 by the magnetic force. At that time, the spring 20 is first compressed, the valve body 17 is displaced toward the compression chamber 14, and the seal ring 18 is brought into contact with the end wall 12 of the piston 11. Thereafter, the piston 11 is further displaced toward the compression chamber 14, and air in the compression chamber 14 begins to be compressed. In this compression initial stage, the second one way valve 31 is closed by the spring force of the spring 34. Then, when the pressure in the compression chamber 14 is slightly increased to reach the predetermined value, the second one way valve 31 is opened. Thereby, the air in the compression chamber 14 is led into the nozzle fitting member 35 through the flexible tube 36, and is blown toward the eye 38 to be examined at the eye-examining position through the nozzle 37.

Even when vibrations due to the driving force of the linear DC motor 23 is transmitted to the cylinder 10 on blowing air in such a manner, the vibrations are absorbed by the flexible tube 36 and not transmitted to the nozzle fitting mumber 35. Thus, the nozzle 37 is not vibrated, and the air stream blown from the nozzle 37 is accurately blown upon a desired location of the eye to be examined at the eye-examining position.

On the other hand, as the piston 11 is displaced toward the compression chamber 14, the inside of the air open chamber 15 is depressed, so that the atmosphere is sucked into the air open chamber through the communicating path 28 after being cleaned by the filter 29.

When the magnetic polarity of the bobbin 24 is made identical with that of the rod 26 by reversing the energizing direction of the coil 25 of the linear DC moter 23, the rod 26 is attracted toward the bobbin 24 by the magnetic force. At that time, the valve body 17 is first displaced toward the air open chamber 15 with respect to the piston 11, the seal ring 18 released from the end wall 12 of the piston 11, and the cylindrical portion 19a of the stopper 19 is brought into contact with the lower end of the large diameter hole portion 13a. Thereby, the compression chamber 14 is communicated with the air open chamber 15 through the slits 22 and the stepped hole 13. Thereafter, the rod 26 is further displaced toward the bobbin 24, and the piston 11 is displaced toward the air open chamber 15. As a result, the compression chamber 14 is depressed, and air in the air open chamber 15 is flown into the compression chamber 14 through the slits 22 and the stepped hole 13. In addition, at this time, since the second one way valve 31 is maintained closed due to the depression of the compression chamber 14, air is not sucked into through nozzle 37.

What is claimed is:

1. A gas stream blower for a non-contact type tonometer comprising:
   (a) a cylinder body;
   (b) a piston slidably arranged in said cylinder body and dividing said cylinder body into an open gas chamber and a compression chamber, said piston including an end wall having a first aperture therein for flow communicating said open gas chamber and said compression chamber;

(c) actuator means for reciprocating said piston in said cylinder body such that said piston alternately cycles between a compression and an intake stroke, said actuator means including a piston rod having a top portion;

(d) a first one-way valve having a valve body including a base portion fitted on said top portion of said piston rod, and an axial portion extending from said base portion, said axial portion being slidably inserted into said first aperture of said piston;

(e) a stop portion, having a diameter larger than said first aperture, connected to a distal end of said axial portion of said first valve to limit movement of said axial portion through said first aperture, said stop portion having at least one second aperture for communicating said open gas chamber and said compression chamber through said first aperture;

(f) sealing means for sealing said first aperture in response to movement of said piston, said sealing means being operably associated with said first one-way valve such that said first aperture is sealed as said piston is moved a first distance from bottom dead center;

(g) a nozzle for ejecting compressed gas within said compression chamber toward an eye-examining position;

(h) a communicating path for flow communicating said compression chamber and said nozzle;

(i) a second one-way valve positioned in said communicating path between said compression chamber and said nozzle to permit gas flow from said compression chamber to said nozzle, said second one-way valve being opened in response to a predetermined pressure of the compressed gas in said compression chamber;

(j) said cylinder body having a gas suction hole communicating said open gas chamber and atmosphere; and (k) a filter disposed in said gas suction hole for filtering gas drawn into said open gas chamber.

2. The gas stream blower according to claim 1, wherein said actuator is a linear actuator arranged coaxially relative to said piston and within said open gas chamber.

3. The gas stream blower according to claim 2, wherein said linear actuator comprises an electro-magnetic actuator including a bobbin inserted through an end portion of said cylinder body on said open gas chamber side, and a rod-shaped permanent magnet connected to said piston forwardly and rearwardly movable within said bobbin in response to current flowing through an electric coil disposed around of said bobbin.

4. The gas stream blower according to claim 1, wherein the path communicating the compression chamber and the nozzle includes a flexible tube portion.

5. The gas stream blower according to claim 4, wherein said second one-way valve includes a valve cylinder having a distal end portion, and one end of said flexible tube portion being communicated with said nozzle and the other end of said flexible tube portion being connected to said distal end portion of said valve cylinder.

6. The gas stream blower according to claim 1, wherein said end wall of said piston includes a cylindrical recess having a bottom surface formed on said compression chamber side, said first aperture being formed in said bottom surface, and wherein said stop portion includes a top wall and a cylindrical sidewall extending axially from said top wall, said sidewall being dimensioned to fit in said cylindrical recess and said second aperture being formed in said sidewall.

7. A gas stream blower for a non-contact type tonometer according to claim 1, wherein said compression chamber of said cylinder body includes a top wall having an opening therein for ejecting the compressed gas from the compression chamber, and wherein, said second one-way valve comprises:

(a) a valve cylinder disposed on a top surface of said top wall of said compression chamber, said valve cylinder including a first cylindrical sidewall having a first diameter, and a second cylindrical sidewall having a second diameter smaller than said first diameter, and a stepped wall portion connecting said first cylindrical sidewall with said second cylindrical sidewall, said first cylindrical sidewall being disposed proximate said top wall of said compression chamber;

(b) a cylindrical valve body, including an end wall, dimensioned to slidably fit within said second cylindrical sidewall, said end wall of said valve body being positioned proximate said opening in said top wall of said compression chamber and having a diameter larger than said opening to seal said opening;

(c) a spring interposed between said end wall of said cylindrical valve body and said stepped wall portion of said valve cylinder to bias said end wall of said cylindrical valve body against the top surface of said top wall of said compression chamber to seal said opening of said top wall;

(d) a communicating hole positioned in said sidewall of said cylindrical valve body for passing gas from said compression chamber into said nozzle as said spring is compressed to lift said end wall off said opening.

8. The gas stream blower according to claim 1, wherein said gas is air.

* * * * *